(12) United States Patent
Ranch et al.

(10) Patent No.: US 8,334,429 B2
(45) Date of Patent: Dec. 18, 2012

(54) **AUXOTROPHIC *AGROBACTERIUM* FOR PLANT TRANSFORMATION AND METHODS THEREOF**

(75) Inventors: Jerome P. Ranch, West Des Moines, IA (US); Matthias Liebergesell, Kennett Square, PA (US); Carl W. Garnaat, Eureka, MO (US); Gary A. Huffman, Des Moines, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 332 days.

(21) Appl. No.: 12/650,106

(22) Filed: Dec. 30, 2009

(65) Prior Publication Data

US 2010/0186122 A1 Jul. 22, 2010

Related U.S. Application Data

(60) Provisional application No. 61/141,967, filed on Dec. 31, 2008.

(51) Int. Cl.
*C12N 15/84* (2006.01)
*C12N 15/74* (2006.01)
*C12N 1/20* (2006.01)
*C12N 1/21* (2006.01)

(52) U.S. Cl. .............. 800/294; 800/320; 800/320.1; 435/252.2; 435/424; 435/430.1; 435/431; 435/469; 435/477

(58) Field of Classification Search .................. None
See application file for complete search history.

(56) References Cited

U.S. PATENT DOCUMENTS

| 6,323,396 | B1 | 11/2001 | Dirks et al. |
| 6,740,526 | B1 | 5/2004 | Curtis |
| 2002/0061579 | A1 | 5/2002 | Farrand et al. |

FOREIGN PATENT DOCUMENTS

| DE | 42 31 764 A1 | 3/1994 |
| WO | WO 99/10512 A1 | 3/1999 |
| WO | WO 2006/003018 A2 | 1/2006 |

OTHER PUBLICATIONS

Ahmad, et al., "Thymine Metabolism and Thymineless Death in Prokaryotes and Eukaryotes," *Annu. Rev. Microbiol.*, 1998, vol. 52, pp. 591-625.

Database UniProt [Online] "RecName: Full=Thymidylate synthase; Short=TS; Short=TSase; EC=2.1.1.45," 2002, XP002572646.

Demarre, et al., "A new family of mobilizable suicide plasmids based on broad host range R388 plasmid (IncW) and RP4 plasmid (IncPα) conjugative machineries and their cognate *Escherichia coli* host strains," *Research in Microbiology*, 2005, vol. 156, pp. 245-255.

Wong, et al., "Efficient and seamless DNA recombineering using a thymidylate synthase A selection system in *Escherichia coli*," *Nucleic Acids Research*, 2005, vol. 33(6), pp. 1-9.

Collens, Jason I., et al., "Development of Auxotrophic *Agrobacterium tumefaciens* for Gene Transfer in Plant Tissue Culture", Biotechnol. Prog., 20:890-896 (2004).

Reyrat, Jean-Marc, et al., "MiniReview, Counterselectable Markers: Untapped Tools for Bacterial Genetics and Pathogenesis", Infection and Immunity, 66(9):4011-4017 (1998).

Steidler, Lothar, et al., "Biological containment of genetically modified *Lactococcus lactis* for intestinal delivery of human interleukin 10", Nature Biotechnology, 21(7):785-789 (2003).

*Primary Examiner* — David T Fox
(74) *Attorney, Agent, or Firm* — Pioneer Hi Bred Int'l., Inc.

(57) ABSTRACT

Auxotrophic *Agrobacterium* and methods employing auxotrophic *Agrobacterium* are provided. Auxotrophic *Agrobacterium* may be used in a variety of methods including biologically containing *Agrobacterium* comprising a transgene and transforming a plant cell without using an *Agrobacterium* counter-selective agent. Transforming maize immature embryos using an *Agrobacterium* auxotrophic for thymidine results in comparable transformation efficiency as transformation achieved using prototrophic *Agrobacterium*. Methods for producing an *Agrobacterium* thymidine auxotroph and using the auxotroph in transformation methods are disclosed. Transformed tissues and plants produced using methods of the present invention are also provided.

32 Claims, 6 Drawing Sheets

```
CGAATTCCCGCACCGCCATTAGGCAGCGAGAGCGTATTCCTTAGCGTTGTTGTCATTTGCAACTA
CACTTGTGACCCGATAACGGCGGTATCATGCCGAGCAAAAGTTCGATCTTTACGCCCTTGTCGAT
CCTATTTCGCCCCCATCAAAAGCCGGCCTTCATCTTCAAAAGCCGCCGGTTTTTGGTGGAGGCGC
CGGGTACCGCCCCCGGGTCCAATAGGTTTATTACACCGACCGTTTATCGCCATAGCCGGGTTGCC
CCGGCAAGGTTCATATAGGCGTTTCCCTTGGCCGAGAAAAGGGGCCGATGACAATTCCATGAAAA
GATTTCGTGTTTGCCGCCCACAATTTAGACAATTCTTGACGACGAGGGATTGCTGACACATTCTC
CCTACAACCGGTCACCACAAGCAACACCGGGCCGGGGACACACGAAGGAGTGGACATGACTGACT
ATCTCGCAGATGTGAAGAAATACGACGCAGCAGCCGACGAAGCGATTGTCGGCAAGATCGTCAAA
CATCTCGGCATTGCCCTGCGCAACCGGGATTCATCGTTGGTGTCCGCTTCCGATCCGGAAGAGCT
TGCACGTGTGAAGGCGAACTGGTGCGGCAAGAAGCTTGGCGTGACCGATGACAGCGCCGACAAGG
CGATCGATGCAACCGCCAAGGCCATGGCCGCAGACCGCTCCAAGTCGCGTGTGACGTTTTATTAT
CTGGTGGCCAAGGAACTGGGCAAACTCCAGTCGCTCTGATTTTTTGGCGGGGATAAGCGACCCGC
TGGTGATTGGTTCTGTCGCCCTGTGTTATTATATTCCCTTGATATCAGGGAATCGGCGGCAGAAC
ACATGAAACAATATCTCGATCTTCTCCGGCATGTGATGGAAACCGGCTCCGACCGCGGAGA//GC
CTTGCCGACCATGCGCCTCAACCCGGATGTACGAGACCTCTTCTCCTTTAAGTTCGAAGACTTTA
CGCTGGAGAACTACGAGGCGGATTCAACCATCAAGGCACCGATCGCGGTATGAGCGAGCCGCGCA
TCACCATCATCGTCGCGGTGTCGGAAAACGGCGTTATCGGCCGCGACCTCGATATGCCTTGGAAG
CTTTCCACTGACCTAAAGCGCTTCAAGGCGATGACGATGGGCAAACCGCTCATCATGGGCAGGAA
GACATTTCTCTCGGTGGGCGAGCGTCCATTGCCGGGCCGGCCGCACATCATCGTCAGCCGCAATG
CCGATTACAGGCCTGATGGCGTGGATGTCGTGTCGTCGCTTGAAGACGCCCTCGCGCTTGGCAAA
AGCAAGGCTGCGGAACTGGGTGTGGACGAGGTTTTCGTTGCCGGTGGCGGGGAAATCTACCGTCA
GGCCATGCCGTTTGCCGATCAACTTTCCGTCACCCATGTGGCCGTAAAGCTTGATGGCGACACTT
TTTTTCCGGAAATCGATCCCGCCGTCTTTGAAAAAATCGAGGAAAATGCCGTTCCCGCCGGGGAA
AAGGACAATTATCCGGTTCTGTTCACCACTTATTTGCGCAGAGCCGCGTCAAAGTGAACTATTTA
CCCTGATTGGGTATTTAGTTACCACCTCTGCGTTGAAACGCACGCTTCTCCTTCTTATAACGGGT
CCATATTCCCGCCGCACGCGAGCAATCGCTTTCGAACGGGATCGGGAGAGGCTTTTATAAAGAGG
TATTGATGCCCTGGAGCAATCAGAATGGCGGCGGCGGCCCTTGGGCGGCGGCGGTGGTGGCGGA
AACAACCAGGGCGGCGGTGGCGGCCCATGGAGGCAGGGG (SEQ ID NO:11)
```

*FIG. 1*

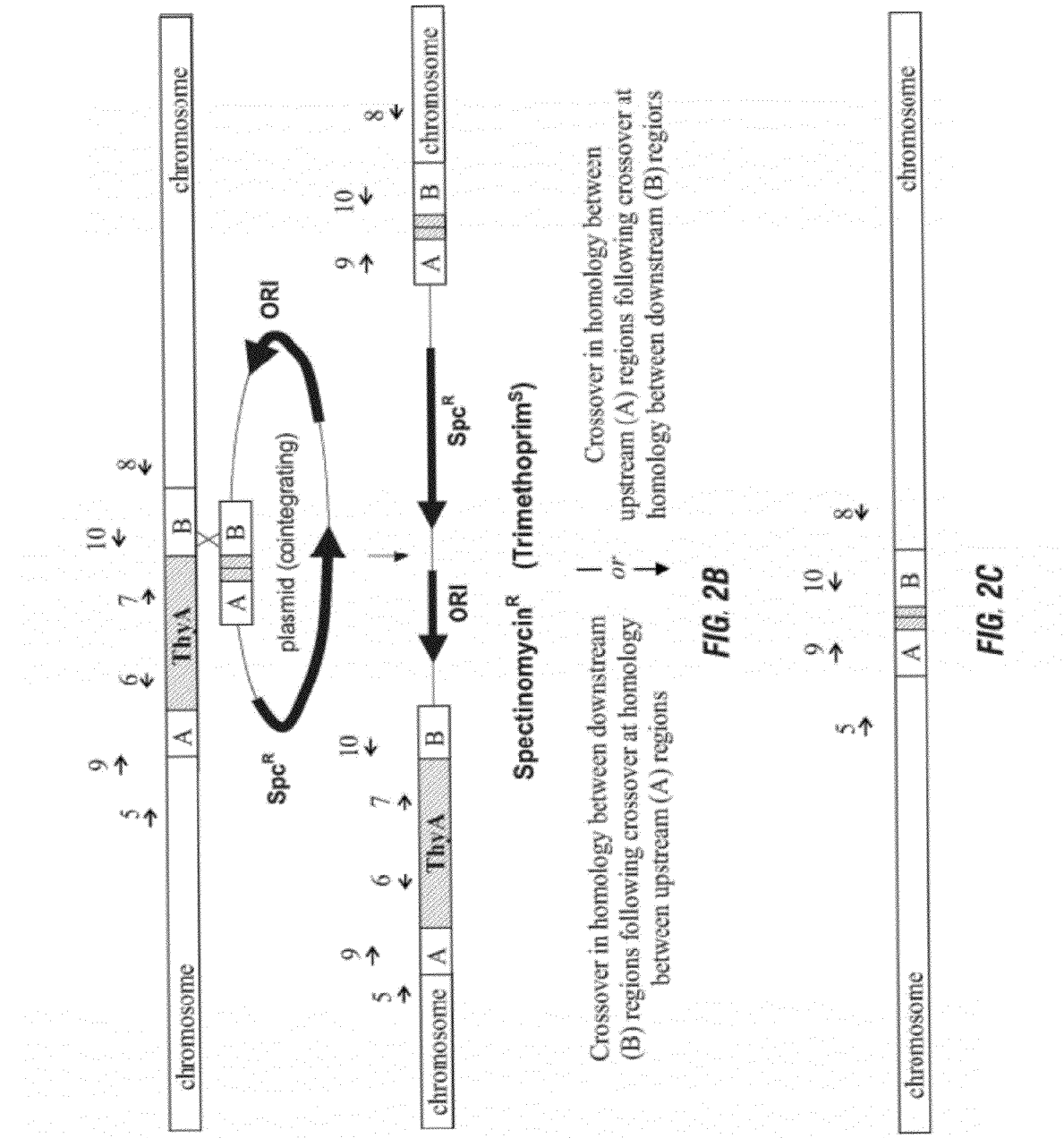

| Agrobacterium genotype | Protocol | Transformation Frequency | % Single Copy | Avg Seed |
|---|---|---|---|---|
| PHP15325 (control) | Standard | 0.26 (115/429) | 42/81 (51%) | 164 |
| PHP30894 (thymidine auxotroph) | Improved | 0 (0/495) | | |
| PHP30894 (thymidine auxotroph) | Improved + thymidine | 0.23 (101/437) | 32/71 (45%) | 159 |

$\chi 2= 0.7$, 1 df, ns

*FIG. 5*

AUXOTROPHIC *AGROBACTERIUM* FOR PLANT TRANSFORMATION AND METHODS THEREOF

CROSS-REFERENCE TO RELATED APPLICATIONS

This application claims priority under 35 U.S.C. §119 of provisional application Ser. No. 61/141,967 filed Dec. 31, 2008, and which application is hereby incorporated by reference in its entirety.

FIELD OF THE INVENTION

This invention relates to auxotrophic *Agrobacterium* and to the use of an *Agrobacterium* auxotroph in the stable genetic transformation of plant cells.

BACKGROUND OF THE INVENTION

*Agrobacterium* is a genus of soil Gram-negative bacteria that is widely used for the introduction of exogenous DNA into plants. The use of *Agrobacterium* species for DNA transfer is based on their natural ability to transfer DNA sequences into the genomes of plants. The most widely used species of *Agrobacterium* is *A. tumefaciens* the causal agent of the neoplastic disease crown gall in plants. A closely related species, *A. rhizogenes*, induces hairy root disease and also has been used for DNA transfer to plant genomes, but to a lesser extent. The ability of these bacteria to transfer DNA into plants depends on the presence of large plasmids (>100 kb) within the cells. These plasmids are referred to as the Ti (Tumor inducing) or Ri (Root inducing) in *A. tumefaciens* and *A. rhizogenes*, respectively. A third species, *A. radiobacter*, differs in lacking a Ti or Ri plasmid. The mechanism for DNA transfer from the bacterium into the plant genome involves the mobilization of specific T-DNA (transfer DNA) molecules from the Ti plasmid into the host cell. The T-DNA region is delineated by 25 by referred to as the left and right borders. In pathogenic *Agrobacterium* cells, within the T-DNA element reside genes for the over production of auxins and cytokinins which manifest the crown gall symptoms. The T-DNA element of pathogenic *Agrobacterium* strains also contains genes for the production of opines that are utilized by the bacterium as a nitrogen source.

*Agrobacterium*-mediated DNA transfer to plant cell genomes is usually conducted with "disarmed" (auxin, cytokinin and opine gene sequences removed from the T-DNA element) strains. In transformation studies, sequences of interest are introduced into the T-DNA region of a "disarmed" *Agrobacterium* strain. This chimeric T-DNA element can be carried on a separate, smaller, wide host range plasmid referred to as a binary vector or directly introduced into the resident "disarmed" Ti plasmid. The first step in the basic *Agrobacterium*-mediated transformation protocol requires the inoculation of plant cells with transconjugants of "disarmed" *Agrobacterium* cells carrying the sequences of interest on the chimeric T-DNA element. The plant cells are subsequently cultured for a period generally ranging from one to seven days in a step of the protocol referred to as co-cultivation. Following the co-cultivation period, the plant cells are subcultured on regeneration medium for further plant development.

It is common practice in *Agrobacterium* transformation processes of plants to use an *Agrobacterium* counter-selective agent, such as an antibiotic, in the plant culture medium post co-culture as a strategy to counter-select *Agrobacterium* cells. Counter-selection is used to cure the plant tissue of the *Agrobacterium*. Without curing, the *Agrobacterium* would rapidly overgrow and kill the plant tissue, thereby resulting in the production of few or no transgenic events. Furthermore, different strains of *Agrobacterium* are differently affected by different counter-selective agents, see for example, Ogawa, Y., et al., *Screening for highly active beta-lactam antibiotics against Agrobacterium tumefaciens*, Arch Microbiol, 181(4): 331-6 (2004). Some counter-selective agents have biocidal effects, while others are biostatic. Similarly, plant cell and tissue cultures may have varied responses to bacterial counter-selective agents (for example; Ling, H. Q., et al., *Effect of ticarcillin/potassium clavulanate on callus growth and shoot regeneration in Agrobacterium-mediated transformation of tomato (Lycopersicon esculentum Mill.)* Plant Cell Reports, 17:843 (1998); Tang, H., et al., *An evaluation of antibiotics for the elimination of Agrobacterium tumefaciens from walnut somatic embryos and for the effects on the proliferation of somatic embryos and regeneration of transgenic plants*, Plant Cell Reports, 19:881 (2000); Alsheikh, M. K., et al., *Appropriate choice of antibiotic and Agrobacterium strain improves transformation of antibiotic-sensitive Fragaria vesca and F. v. semperflorens*, Plant Cell Reports, 20:1173 (2002). While some bacterial antibiotics are toxic to plant cell cultures, others may have plant growth regulator activity (for example, Borrelli, G. M., et al., *Effect of cefotaxime on callus culture and plant regeneration in durum wheat*, Journal of Plant Physiology, 140:372 (1992); Lin, J. J., et al., *Plant hormone effect of antibiotics on the transformation efficiency of plant tissues by Agrobacterium tumefaciens cells*, Plant Science (Limerick), 109:171 (1995). In the development of any plant transformation protocol via *Agrobacterium*, it is of importance to use a counter-selective agent that effectively kills the *Agrobacterium*, but has no undesired effect on the plant tissue (Shackelford, N. J., et al., *Identification of antibiotics that are effective in eliminating Agrobacterium tumefaciens*, Plant Molecular Biology Reporter, 14:50 (1996). It can be time-consuming and difficult to identify these conditions and one ordinarily skilled in the art must make concessions to achieve an acceptable level of plant transformation efficiency (Ogawa, Y., et al., *Screening for highly active beta-lactam antibiotics against Agrobacterium tumefaciens*, Arch Microbiol, 181(4):331-6 (2004); Ogawa, Y., et al., *Evaluation of 12 beta-lactam antibiotics for Agrobacterium-mediated transformation through in planta antibacterial activities and phytotoxicities*, Plant Cell Rep, 23(10-11): 736-43 (2005). For these and other reasons, there is a need for the present invention.

SUMMARY OF THE INVENTION

It is an object, feature, or advantage of the present invention to provide a method for the transformation and regeneration of plant cells that does not need an *Agrobacterium* counter-selective agent to cure plant tissue of *Agrobacterium*.

Still another object, feature, or advantage of the present invention is to provide an efficient method for the transformation and regeneration of plant cells.

Another object, feature, or advantage of the invention is to provide a method for the transformation and regeneration of plant cells that is less expensive than traditional transformation methods.

Yet another object, feature, or advantage of the present invention is to provide a method for the transformation and regeneration of plant cells that does not employ an *Agrobacterium* counter-selective agent while maintaining or increasing transformation frequency and efficiency.

Another object, feature, or advantage of the invention is to provide a method for the transformation and regeneration of plant cells that does not have an undesired effect on plant cell cultures.

Still another object, feature, or advantage of the present invention is to provide a method for the transformation and regeneration of plant cells that effectively kills *Agrobacterium*.

A further object, feature, or advantage of the invention is to provide a method to biologically contain transgenic *Agrobacterium* used in the transformation and regeneration of plants.

Yet another object, feature, or advantage of the invention is to provide an auxotrophic *Agrobacterium*.

One or more of these and other objects, features, or advantages of the present invention will become apparent from the specification and claims that follow.

According to one aspect of the present invention, a method of transforming a plant cell and regenerating the transformed plant cell in the absence of an *Agrobacterium* counter-selective agent includes contacting a plant cell with *Agrobacterium* that is a thymidine auxotroph in the presence of a compound necessary for the auxotrophic *Agrobacterium*'s survival, proliferation or growth. The auxotroph will exhibit the inability to survive, proliferate or grow in the absence of the compound. Suitable compounds include but are not limited to thymidine or thymine or derivatives thereof in the thymine biosynthesis pathway.

The auxotroph may harbor a transgene, for example, on a binary vector, to enable transfer of the transgene to the plant cell. The thymidine auxotroph may be deficient or disabled for one or more genes involved in the biosynthesis of thymine or in the regulation of this pathway. In one aspect, the thymidine auxotroph has a thymidylate synthase gene that is disrupted, for example, by deletion, partial deletion, knock out, insertion, and/or mutation. The auxotrophic *Agrobacterium* may be from the species *Agrobacterium tumefaciens, rhizogenes* or *radiobacter*. According to another aspect of the present invention, a method of producing an *Agrobacterium* thymidine auxotroph is provided.

Advantageously, the present invention allows for the regeneration of a plant cell, plant part or plant without the use of an *Agrobacterium* counter-selective agent, such as an antibiotic or herbicide. Common counter-selective agents include but are not limited to carbenicillin, cefotaxime, vancomycin, piperacillin, ticarcillin, ceftazidime, cefbuperazone, cefminox, moxalactam, flomoxef, aztreonam, carumonam, or meropenem.

The transfer of the transgene may be facilitated by co-cultivating the plant cell with the thymidine auxotroph in the presence of a compound necessary for the auxotrophic *Agrobacterium*'s survival, proliferation or growth. The transformed plant cell expressing the transgene may be selected for and regenerated in the absence of an *Agrobacterium* counter-selective agent, and in the absence of the compound necessary for the growth of the auxotroph. In the absence of the compound necessary for the auxotroph to survive, the auxotroph dies and a counter-selective antibiotic is not required to cure the plant material of the contaminating *Agrobacterium*. Additionally, the auxotrophic *Agrobacterium* and its use in transforming plant cells permits for the biological containment of *Agrobacterium* carrying transgenes. The auxotroph significantly minimizes or even ablates the potential for the accidental release of genetically engineered organisms.

Other objects, features, advantages and aspects of the present invention will become apparent to those of skill from the following description. It should be understood, however, that the following description and the specific examples, while indicating preferred aspects of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE FIGURES

The invention can be more fully understood from the following detailed description and the accompanying figures.

FIG. 1 shows the nucleotide sequence for a deletion mutant of a ThyA gene of *Agrobacterium tumefaciens* C58 (LBA4404) (SEQ ID NO:11) See also Genbank Accession Nos: NC003062 and AE007869. Underlined sequence is the 5' end of the ThyA gene. The bold sequence is the 3' sequence (after the deletion). Highlighted sequence shows the coding sequence. The double hatch marks (//) indicates where the ThyA gene has been disrupted.

FIGS. 2A-2C are diagrammatic illustration showing the possible integrations of a ThyA deletion clone into the ThyA region of A. tumefaciens, with positions of analytical PCR primer binding sites indicated.

FIG. 5 is a chart comparing the transformation frequency achieved using transformation and regeneration methods with and without a thymidine auxotrophic *Agrobacterium*. Methods are further described elsewhere herein, for example, in Example 4.

DETAILED DESCRIPTION OF THE INVENTION

Figure 2A:
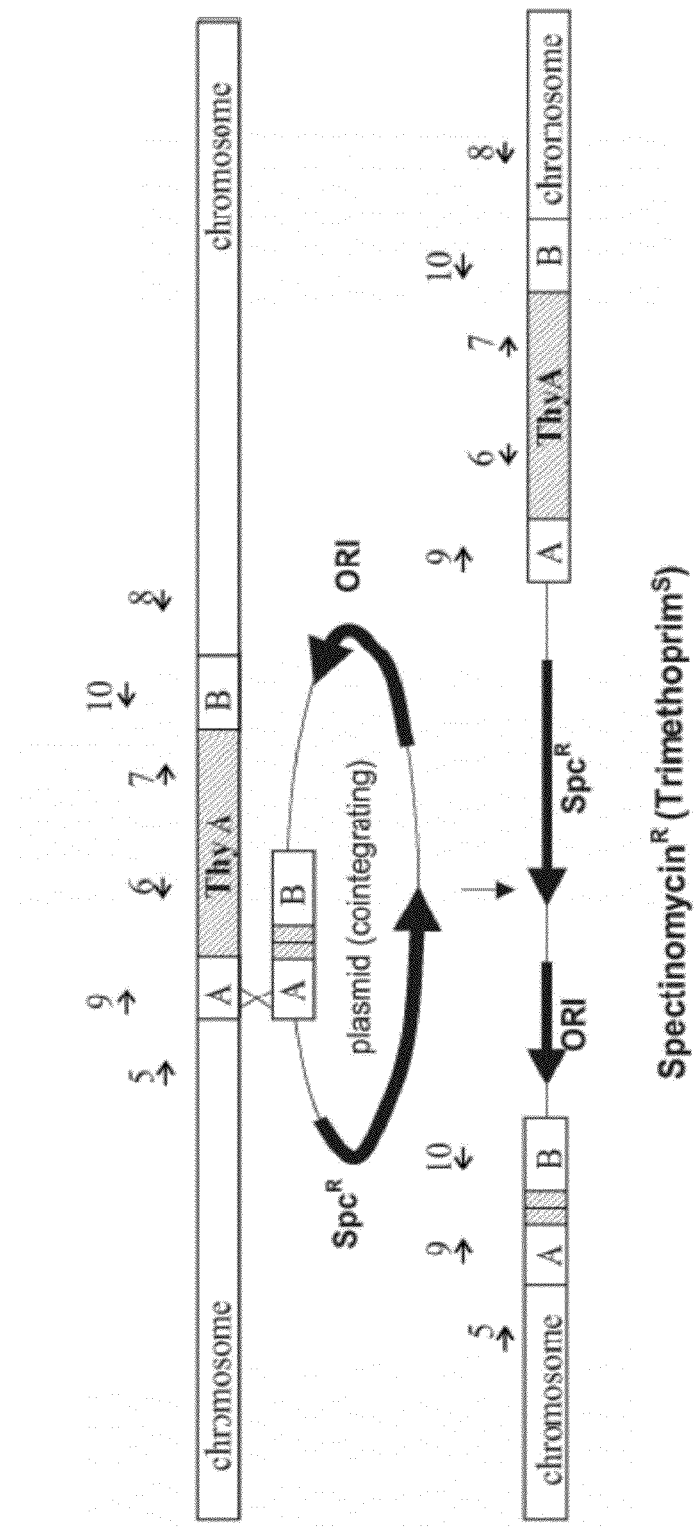

The present invention now will be described more fully hereinafter with reference to the accompanying examples, in which some, but not all aspects of the invention are shown. Indeed, the invention may be embodied in many different forms and should not be construed as limited to the aspects set forth herein; rather, these aspects are provided so that this disclosure will satisfy applicable legal requirements. Like numbers refer to like elements throughout. All publications, patents, patent applications and other references cited in this application are herein incorporated by reference in their entirety as if each publication, patent, patent application or other reference were specifically and individually indicated to be incorporated by reference.

Many modifications and other aspects of the invention set forth herein will come to mind to one skilled in the art to which this invention pertains, having the benefit of the teachings presented in the descriptions and the drawings herein. Therefore, it is to be understood that the invention is not to be limited to the specific aspects disclosed and that modifications and other aspects are intended to be included within the scope of the appended claims. Although specific terms are employed herein, they are used in a generic and descriptive sense only and not for purposes of limitation.

The articles "a" and "an" are used herein to refer to one or more than one (i.e., to at least one) of the grammatical object of the article. By way of example, "an element" means one or more than one element.

Definitions:

As used herein the term "selective agent" is meant to include any compound that can act to permit differentiation between cells transformed with a heterologous sequence, such as a gene that confers resistance to the selective agent, introduced during the transformation process and those cells that were not transformed during the transformation process. The cells may be plant cells or *Agrobacterium* cells. Exemplary selective agents include but are not limited to kanamycin, hygromycin, streptomycin, chloramphenicol, ampicillin, erythromycin, spectinomycin, tetracycline, bialaphos, glyphosate, glufosinate, rifampicin, or dicamba, and the like.

As used herein the term "counter selective agent" is meant to include any compound that can act to kill *Agrobacterium* cells or reduce *Agrobacterium* growth, proliferation or survival on plants, plant cells, or plant tissues. Exemplary counter selective agents include but are not limited to carbenicillin, cefotaxime, vancomycin, piperacillin, ticarcillin, ceftazidime, cefbuperazone, cefminox, moxalactam, flomoxef, aztreonam, carumonam, meropenem, and the like.

As used herein, the term "plant" includes reference to an immature or mature whole plant, including a plant that has been detasseled or from which seed or grain has been removed. Seed or embryo that will produce the plant is also considered to be the plant.

As used herein, the term "plant parts" includes leaves, stems, roots, seed, grain, embryo, pollen, ovules, flowers, ears, cobs, husks, stalks, root tips, anthers, pericarp, silk, tissue, cells and the like.

A "control" or "control *Agrobacterium*" provides a reference point for measuring changes in survival, growth or proliferation of the auxotrophic *Agrobacterium* or in transformation frequency achieved using the auxotrophic *Agrobacterium*.

A control *Agrobacterium* may comprise, for example: (a) a wild-type, prototrophic *Agrobacterium*, i.e., of the same genotype as the starting material for the genetic alteration which resulted in the candidate auxotrophic *Agrobacterium*; (b) the candidate auxotrophic *Agrobacterium* itself, under prototrophic conditions in which the compound necessary for survival, growth or proliferation of the auxotrophic *Agrobacterium* is absent; or (c) the candidate auxotrophic *Agrobacterium* itself, under auxotrophic conditions in which the compound necessary for survival, growth or proliferation of the auxotrophic *Agrobacterium* is present.

The term "transgene," as used herein, refers to the introduction of a desired DNA sequence into a plant cell's genome, including but not limited to genes or DNA sequences which may not normally be present in the plant cell, genes which are present, but not normally transcribed and translated ("expressed") in a given genome, or any other genes or DNA sequences which one desires to introduce into the genome. This may include genes which may normally be present in the non-transgenic genome but which one desires to have altered in expression, or which one desires to introduce in an altered or variant form. The term transgene is also used to describe genetic material which has been or is about to be artificially inserted into the genome of a plant or plant cell.

The present invention relates to the use of an auxotrophic *Agrobacterium* in transforming plant cells. Novel *Agrobacterium* auxotrophs and methods for transforming plant cells are described herein. In particular, auxotrophic *Agrobacterium* of the present invention can be used to generate transgenic plants wherein the presence of auxotrophic *Agrobacterium* in plants, plant cells, or plant tissue is regulated. Accordingly, levels of viable auxotrophic *Agrobacterium* in plants, plant cells, or plant tissue are reduced, if not eliminated, when compared to a control, for example, prototrophic, non-auxotrophic *Agrobacterium*. The present invention also provides methods for biologically containing *Agrobacterium* comprising a transgene by using an auxotrophic *Agrobacterium*.

Another aspect of the invention is based in part on the demonstration that the use of an *Agrobacterium* thymidine auxotroph of the present invention in transforming maize immature maize embryos does not require the use of a counter-selective agent, for example, an antibiotic. Accordingly, the present invention also provides methods of transforming plant cells without antibiotic counter selection by using an auxotrophic *Agrobacterium*. This method also has the advantage of decreasing the presence of viable transgenic *Agrobacterium* in plants or plant tissues generated by transformation techniques that utilize transgenic *Agrobacterium*. Other advantages, benefits or effects from using an auxotrophic *Agrobacterium* are described elsewhere herein.

Auxotrophic *Agrobacterium* of the present invention include *Agrobacterium* that are unable to synthesize one or more compounds required for its growth, proliferation or survival or have an impaired ability to synthesize an amount of a compound required for its growth, proliferation or survival. Examples of auxotrophic *Agrobacterium* include, without limitation, those that are deficient in amino acid, nucleic acid, carbohydrate or vitamin metabolism or combinations thereof. Accordingly, the auxotroph may be disabled or deficient for one or more genes involved in the biosynthesis of a vitamin, DNA, RNA, an amino acid or a carbohydrate in a metabolic pathway or in the regulation of such biosynthetic pathways. Also included are auxotrophic *Agrobacterium* that have one or more genes encoding proteins that regulate a metabolic pathway or participate in a biosynthetic pathway that fail to produce an active protein or a sufficiently active protein such that the *Agrobacterium* is rendered an auxotroph for a particular compound. Examples of such genes include but are not limited to those that indirectly or directly produce or regulate any amino acid such as isoleucine, valine, phenylalanine, arginine, cysteine, histidine, leucine, methionine, proline, threonine, tryptophan; any nucleic acid such as a purine or pyrimidine base, e.g. cytosine, thymine, guanine, thymidine, adenine, uracil, xanthine, hypoxanthine, and 2-aminopurine or any precursor thereof, nucleosides such as cytidine, uridine, adenosine, guanosine, thymidine and inosine; and any vitamin such as thiamine and pantothenate. In one aspect, the *Agrobacterium* auxotroph is a thymidine auxotroph. As used herein, the terms "thymidine auxotroph", "thymidine auxotroph of *Agrobacterium*", "*Agrobacterium* thymidine auxotroph", and/or "thymidine auxotrophic *Agrobacterium*" are used interchangeably and include but are not limited to the examples disclosed herein as well as auxotrophs that have a disruption of a gene that regulates or participates in the thymine synthesis pathway, for example, in metabolic pathways which lead to the synthesis of thymine, so that the *Agrobacterium* is rendered an auxotroph for thymine or thymidine or derivative thereof as demonstrated by the assays disclosed herein. An example of one such gene is thyA, a gene that encodes thymidylate synthase, a protein which converts dUMP to dTMP In one aspect, the Agrobacterium auxotroph is any bacteria belonging to the genus of *Agrobacterium* that is auxotrophic for at least one particular compound and is capable of transferring one or more transgenes to a plant cell. Any suitable species or strain of the genus *Agrobacterium* may be used in the present invention. In one aspect, the *Agrobacterium* is an *Agrobacterium* belonging to the species rhizo genes or *tumefaciens*. In one aspect, the *Agrobacterium* is the strain LBA4404, EHA101, C58, EHA105, AGL1, or GV3101 and the like. *Agrobacterium tumefaciens* LBA4404thy of the invention was deposited with the Patent Depository of the American Type Culture Collection (ATCC), 10801 University Blvd., Manassas, Va., 20110-2209 on Dec. 15, 2009 and assigned Patent Deposit No. PTA-10531. Accordingly, compositions include the auxotrophic *Agrobacterium* ThyA knock-out, LBA4404thy-, deposited as Patent Deposit No. PTA-10531. This deposit will be maintained under the terms of the Budapest Treaty on the International Recognition of the Deposit of Microorganisms for the Purposes of Patent Procedure. This deposit was made merely as a convenience for those of skill in the art and are not an admission that a deposit is required under 35 U.S.C. §112. The LBA4404thy- deposited with the ATCC on Dec. 15, 2009 were taken from the deposit maintained by Pioneer Hi-Bred International, Inc., 7250 NW 62nd Avenue, Johnston, Iowa 50131-1000. Access to this deposit will be available during the pendency of the application to the Commissioner of Patents and Trademarks and persons determined by the Commissioner to be entitled thereto upon request.

Suitable auxotrophic *Agrobacterium* for use with the methods of the present invention includes but is not limited to those that are naturally occurring, i.e. spontaneous auxotrophs, and those that are generated. Candidate auxotrophic *Agrobacterium* may be generated by any number of suitable techniques and approaches, including, for example, chemical induction of mutations, for example, by chemically treating *Agrobacterium* with nitrosoguanidine or ultraviolet irradiation to induce mutants, or genetic engineering using recombinant DNA techniques. Such techniques include but are not limited to, transformation, transfection, conjugation, site-directed mutagenesis, and other techniques by which foreign nucleic acid molecules can be introduced into the *Agrobacterium* and "knock out" or disrupt a target gene or gene product, for example, through deletions, insertions, and substitutions of the target gene or partial gene sequence so that expression is disrupted. Deletion of the target sequence or gene in the *Agrobacterium* genome is preferred to reduce the occurrence of reversions.

One approach of deleting, inserting or substituting the target gene is through the use of a nucleic acid construct comprising a knock-out of the target gene or a fragment thereof. Nucleic constructs may be produced using methods well known to those of ordinary skill in the art which can be found, for example, in standard texts such as Sambrook et al. Molecular Cloning, $2^{nd}$ edition, Cold Spring Harbor Laboratory Press, 1989 and Ausubel, et al. Short Protocols in Molecular Biology, 3rd ed., Wiley & Sons, 1995. In one aspect, the nucleic acid construct comprises at least two sequences that are homologous to all or part of the wild type target gene to enable integration by homologous recombination. In one aspect, the sequences flank all or part of the target gene. In one aspect, the nucleic acid construct contacts the chromosomal DNA of the *Agrobacterium* comprising a wild-type target gene under conditions that permit homologous recombination between the nucleic acid construct and the wild-type target gene. Depending on the homologous sequences used, homologous recombination between the nucleic acid construct and the wild-type target gene may result in the integration of the nucleic acid construct into the Agrobacterial chromosome adjacent to or within the wild type gene or locus. As a result of the homologous recombination and integration, all or part of the *Agrobacterium* wild type target gene may be removed from the *Agrobacterium* chromosome. The procedures for disrupting the ThyA gene of LBA4404 is described in detail in Example 1 herein. These techniques are readily applicable to disrupting ThyA genes of other *Agrobacterium* species and strains.

Alternatively, in one aspect, the nucleic acid construct that is integrated into the *Agrobacterium*'s chromosomal DNA comprises a selectable marker gene linked to the polynucleotide sequence that targets one or more genes involved in the biosynthesis of a vitamin, DNA, RNA, an amino acid or a carbohydrate in a metabolic pathway or in the regulation of such biosynthetic pathways. Suitable selectable marker genes include any gene that confers a phenotype to the *Agrobacterium* so that transformed *Agrobacterium* having a selectable marker gene integrated into its DNA may be identified. Exemplary selectable marker genes include but are not limited to reporter genes, visual marker genes such as green fluorescent protein (GFP), luciferase, secreted alkaline phosphatase (SEAP), beta-galactosidase and the like, and antibiotic resistance genes, such as kanamycin, streptomycin, carbenicillin, chloramphenicol, ampicillin, erythromycin, tetracycline, or spectinomycin. In addition to screening, the selectable marker genes also allow for maintaining selection pressure on the transformed *Agrobacterium* population to ensure that the introduced nucleic acid construct is retained by the transformed *Agrobacterium*. Accordingly, the candidate auxotrophic *Agrobacterium* may be subjected to conditions that permit selection of *Agrobacterium* having the selectable marker gene integrated into the Agrobacterial chromosomal DNA. For example, if the selectable marker gene encodes a peptide conferring resistance to a particular antibiotic, the candidate *Agrobacterium* may be subjected to that antibiotic.

In one aspect, the *Agrobacterium* may be subjected to conditions that permit selection of those that are auxotrophic. One skilled in the art will appreciate that candidate auxotrophic *Agrobacterium* may be evaluated using routine techniques, including culturing the candidate auxotrophic *Agrobacterium* in an environment, for example, medium or soil, that supports prototrophic growth and supplementing the environment with a compound that the auxotroph needs for survival, growth, or proliferation. The survival, growth, or proliferation of the candidate auxotrophic *Agrobacterium* subjected to the prototrophic conditions may be determined in the presence and/or absence of the compound. See, for example, Example 3 which describes a candidate *Agrobacterium* thymidine auxotroph having its thymidylate synthase gene knocked out was tested for ability to grow in the presence or absence of thymidine. The auxotrophic *Agrobacterium* may be grown in any suitable medium such as but not limited to Nutrient broth, AB minimal broth and the like. Assays available for the detection of *Agrobacterium* growth include but are not limited to cell counts, cell activity, cell mass, for example, by using optical density or turbidity. See for example, Pelczar, J., et al., *Microorganisms—Bacteria, Quantitative Measurement of Growth*, in *Microbiology*. McGraw-Hill Book Company: New York (1986), herein incorporated by reference in its entirety. Decreased or no survival, growth, or proliferation of the candidate auxotrophic *Agrobacterium* in the absence of the compound but the existence of or increased survival, growth, or proliferation of the candidate auxotrophic *Agrobacterium* in the presence of the compound indicates that candidate is auxotrophic.

Antibiotics are used in *Agrobacterium* transformation processes to cure the target plant tissue culture of residual *Agrobacterium*. Because the bacteria grows more rapidly than plant cells, plant material would be rapidly killed by the *Agrobacterium*. While the most effective antibiotics kill or retard *Agrobacterium* growth, they are frequently toxic to plant growth, so there remains a balance that must be empirically resolved between an amount effective to kill the *Agrobacterium* and an amount which causes the least amount of damage to the plant tissue. Frequently this results in less than complete kill of *Agrobacterium* resulting in the presence of a small residual amounts of viable *Agrobacterium* in transformed plant tissue and plants regenerated from transformed plant tissue (Mogilner, N., et al., *The persistence of engineered Agrobacterium tumefaciens in agroinfected plants*, Molecular Plant Microbe Interactions, 6(5):673-675 (1993); Landsmann, J., et al., *Elimination of agrobacteria from transgenic plants*, in *Methods for risk assessment of transgenic plants: 3. Ecological risks and prospects of transgenic plants, where do we go from here? A dialogue between biotech industry and science*, K. Ammann, Jacot, Y., Kjellsson, G., Simonsen, V., Editor. Birkhauser Verlag AG: Basel. 63-67 (1999). The residual *Agrobacterium* in the plant is not known to be transmitted to progeny (Landsmann, J., et al., *Elimination of agrobacteria from transgenic plants*, in *Methods for risk assessment of transgenic plants: 3. Ecological risks and prospects of transgenic plants, where do we go from here? A dialogue between biotech industry and science*, K. Ammann, Jacot, Y., Kjellsson, G., Simonsen, V., Editor. Birkhauser Verlag A G: Basel. 63-67 (1999). It is speculated that the residual *Agrobacterium* cells in plant tissues may result from *Agrobacterium* that survive the applied counter-selective agent or are protected from the applied counter-selective agent by surrounding transformed *Agrobacterium* cells. The presence of *Agrobacterium* raises concerns of the potential for accidental release of genetically engineered organisms into the environment if regenerated plants are directly released. Advantageously, in one aspect, the present invention provides a method of biologically containing *Agrobacterium* harboring one or more transgenes of interest.

Advantageously, in one embodiment, the present invention includes an auxotrophic *Agrobacterium* that is genetically disabled and can be eliminated after infection and co-culture without the need for antibiotics. One way to accomplish this is through the use of a thymidine auxotroph of *Agrobacterium*. Because thymidine is not generally included in plant cell culture medium formulations for *Agrobacterium* transformation, culture media during infection and co-culture must be supplemented with thymidine to allow the *Agrobacterium* to perform its gene transfer process. After T-DNA delivery, however, thymidine can be omitted from the plant culture media and remaining *Agrobacterium* eliminated.

Figure 4:
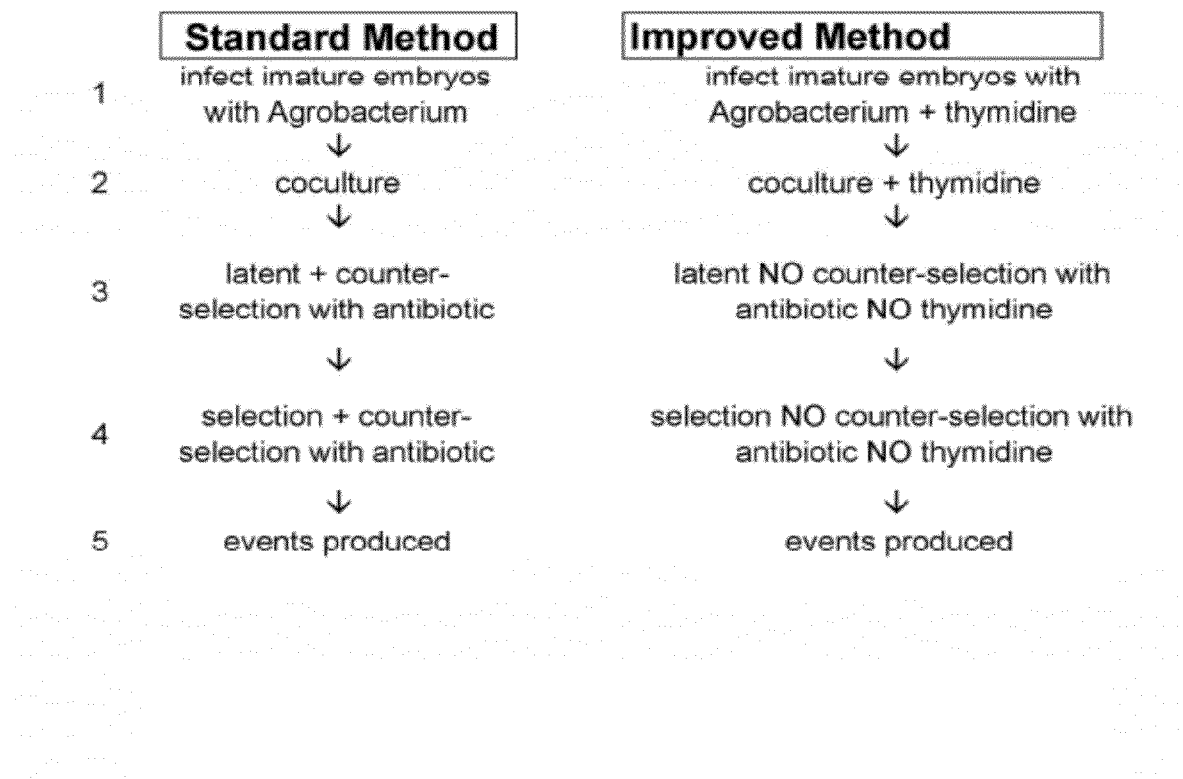
FIG. 4 is a schematic comparing the steps used in one embodiment of a method of the present invention to those used in standard plant transformation and generation methods.

Therefore, as shown in step 3 of FIG. 4, the Standard Method requires the addition of a counter-selective agent, e.g. antibiotic, to cure the plant tissue of remaining *Agrobacterium*. In contrast, as shown in step 3 of FIG. 4, Improved Method, one embodiment of a method of the present invention does not include a counter-selective agent e.g. antibiotic, as the *Agrobacterium* auxotroph dies as a result of nutritional deficiency.

In certain embodiments the auxotroph contains a transgene that confers the desired phenotype to a plant cell. Such transgenes include but are not limited to those that confer abiotic stress tolerance, traits desirable for animal feed, traits desirable for insect, disease or herbicide resistance, traits desirable for processing or process products such as high oil (e.g., U.S. Pat. No. 6,232,529); modified oils (e.g., fatty acid desaturase genes (U.S. Pat. No. 5,952,544; WO 94/11516); modified starches (e.g., ADPG pyrophosphorylases (AGPase), and agronomic traits for traits such as male sterility, stalk strength, flowering time, or transformation technology traits such as cell cycle regulation or gene targeting (e.g. WO 99/61619; WO 00/17364; WO 99/25821).

Accordingly, in one aspect, the method comprises transforming a plant cell using an auxotrophic *Agrobacterium* comprising one or more transgenes of interest. In one aspect, the method includes transforming a plant cell using an auxotrophic *Agrobacterium* comprising one or more transgenes of interest in the presence of a compound required for the auxotrophic *Agrobacterium*'s growth, proliferation or survival. Transforming the plant cell using the auxotroph is typically carried out for a time which is sufficient for transfer of T-DNA from the auxotrophic *Agrobacterium* into the plant cell. The construction of auxotrophic *Agrobacterium* suitable for use with the method of the present invention has been described elsewhere herein.

In one aspect, the plant cell is an immature embryo, for example, an immature embryo from maize. Using the present methods and LBA4404Thy- auxotrophic *Agrobacterium*, immature embryos of maize hybrids and inbreds were transformed and no significant differences observed in transformation frequency between the transformation experiments using auxotrophic *Agrobacterium* and prototrophic LBA4404 *Agrobacterium* control. The plant cell to be transformed may be dicotyledonous or monocotyledonous, including but not limited to sorghum, maize, rice, wheat, soybean, sunflower, canola, alfalfa, barley, or millet cells. Accordingly, in one aspect, the method includes contacting the plant cell with the auxotrophic *Agrobacterium* in the presence of the compound required for the auxotrophic *Agrobacterium*'s growth, proliferation, or survival for a time sufficient for transfer of T-DNA into the plant cell to occur. Without wishing to be bound by this theory, it is believed that the presence of the compound will allow the auxotrophic *Agrobacterium* to perform its gene transfer process. After transgene delivery, often through a T-DNA vector, the mixture of the transformed plant cells and auxotrophic *Agrobacterium* may be exposed to an environment that lacks the compound or sufficient levels of the compound necessary for the auxotroph's growth, proliferation, and/or survival. For example, the mixture of the transformed plant cells and auxotrophic *Agrobacterium* may be exposed to plant culture media where the compound necessary for the auxotroph's growth, proliferation, and/or survival has been omitted.

In one aspect, the method does not include using an *Agrobacterium* counter-selective agent to kill or reduce the growth, proliferation or survival of *Agrobacterium* harboring one or more transgenes in plant tissue, as is typically used after the infection and/or co-cultivation steps, for example, during the regeneration phase. In contrast, the present invention includes, in one aspect of its method, exposing the transformed plant cell to an environment that lacks a sufficient amount of the compound required for the auxotrophic *Agrobacterium*'s growth, proliferation or survival. This allows one to transform a plant cell and generate a plant tissue or plant that expresses the transgene and is substantially free of viable auxotrophic *Agrobacterium* used in the transformation process. For example, thymidine auxotrophic *Agrobacterium* is not viable in environments lacking exogenous thymine or thymidine. As used herein, a plant tissue or plant transformed and regenerated by the methods of the present invention is substantially free of viable auxotrophic *Agrobacterium* when no viable Agrobacterial growth, proliferation or survival are detectable in the plant tissue or plant when measured using optical density, see for example, Pelczar, J., et al., *Microorganisms—Bacteria, Quantitative Measurement of Growth*, in Microbiology. 1986, McGraw-Hill Book Company: New York, herein incorporated by reference in its entirety.

Advantageously, methods of the present invention allow for the biological containment of auxotrophic Agrobacterium comprising a transgene. In one aspect, the method includes contacting the plant cell with a selective agent to select for the transformed plant cell containing the transgene, a step that is typically carried out after co-cultivation. In one aspect, as discussed herein, the transgene is a selectable marker gene or linked to a selectable marker gene that allows for selection by a selective agent. Suitable selectable marker genes include any gene that confers a phenotype to the plant cell so that the transformed plant cell having a selectable marker gene may be identified. Exemplary selectable marker genes include but are not limited to reporter genes, visual marker genes such as green fluorescent protein (GFP), luciferase, secreted alkaline phosphatase (SEAP), beta-galactosidase and the like, and antibiotic resistance genes, such as kanamycin, streptomycin, carbenicillin, chloramphenicol, ampicillin, erythromycin, tetracycline, or spectinomycin. In addition to screening, the selectable marker genes also allow for maintaining selection pressure on the transformed plant cell population to ensure that the introduced transgene, and any controlling promoters and/or enhancers, are retained by the transformed plant cell. Accordingly, the plant cell may be subjected to conditions that permit selection of plant cells having the selectable marker gene. For example, if the selectable marker gene encodes a peptide conferring resistance to a particular antibiotic, the plant cell may be subjected to that antibiotic.

The result of exposing the transformed plant cell to an environment that lacks a sufficient amount of the particular compound required for the auxotrophic Agrobacterium's growth, proliferation, or survival for a sufficient amount of time is the decreased growth or proliferation, or death of the auxotrophic Agrobacterium. Decreased growth or proliferation or death of the auxotrophic Agrobacterium can be determined using any number of assays or techniques, including but not limited to optical density, see for example, Pelczar, J., et al., Microorganisms—Bacteria, Quantitative Measurement of Growth, in Microbiology. 1986, McGraw-Hill Book Company: New York.

In another aspect, the method includes regenerating the transformed plant cell into a transformed plant that expresses the transgene. The plant cell may be stably transformed or transiently transformed. The plant cell may be generated into a plant tissue or callus using any well known method or technique known to one skilled in the art.

Advantageously, methods of the present invention are less expensive than traditional transformation methods, as counter-selective agents, such as antibiotics, are often among the most expensive component of culture media used in transformation. Greater efficiency of transformation is expected as the effect of the antibiotic on plant cells is removed. Without wishing to be bound by this theory, it is believed that an increase in transformation efficiency will result from the removal of the selective agent's adverse affects on plant cells viability.

EXAMPLES

The present invention is further defined in the following Examples, in which parts and percentages are by weight and degrees are Celsius, unless otherwise stated. The disclosure of each reference set forth herein is incorporated herein by reference in its entirety.

Example 1

Construction of a Thymidine Auxotrophic Agrobacterium LBA4404thy−

A strain of Agrobacterium tumefaciens LBA4404 auxotrophic for thymidine, (LBA4404thy−) was created by two sequential homologous recombinations between the native ThyA region and a PCR-generated clone of the region comprising an engineered ThyA deletion. It is understood by one skilled in the art that many possible deletions, variants, etc. could be generated by this and related methods, and the precise specifications of the mutation and details of the protocols described are not meant to be limiting.

Oligonucleotides (SEQ ID NO:1 through SEQ ID NO:4 described elsewhere herein) were obtained from Integrated DNA Technologies, Coralville, Iowa for PCR amplification of a predicted 989 base pair (bp) region extending upstream from the $2^{nd}$ base pair of the $20^{th}$ codon of the published 264 amino acid ThyA-encoding gene of Agrobacterium tumefaciens C58, and a predicted 883 by region extending downstream from the first base pair of the $226^{th}$ codon. Both regions to be amplified included the codon 8-20 region, fused to the codon 226-234 region, encompassed in the oligonucleotides spanning the common region for each amplification. Codons 17-19 of the A. tumefaciens C58 ThyA CDS include a KspI site useful for cloning the two amplified regions together. The common fusion sequences on each fragment added to the predicted upstream and downstream regions gave predicted PCR product sizes of 1013 by and 921 bp, respectively. PCR reactions using LBA4404 (pSB1) (Komari et al, The Plant Journal (1996) 10(1):165-174) total genomic DNA as template and Platinum Pfx DNA polymerase (Invitrogen, Carlsbad, Calif.) generated PCR products consistent with the predicted sizes by agarose gel electrophoresis. The upstream and downstream PCR products were initially cloned into pBluescript SK+(Stratagene, Cedar Creek, Tex.) as KspI/EcoRI and KspI/PCR-blunt-end fragments, respectively and sequenced. Sequencing of the upstream and downstream clones revealed numerous small differences (including a 55 by deletion in the upstream region) compared to the published A. tumefaciens C58 sequence in the vicinity of ThyA, but overall homology was about 84% and 88% respectively.

The downstream clone was joined to the upstream clone at their common KspI site and the resulting ThyA deletion construct was transferred into a derivative of pSB11 (Japan Tobacco, Iwata, Japan) conferring spectinomycin resistance ($Spc^R$) in Agrobacterium. The ThyA deletion $Spc^R$ construct was introduced into A. tumefaciens LBA4404 by electroporation and selection on YEM agar medium (0.4 g/L yeast extract, 10 g/L mannitol, 0.1 g/L NaCl, 0.2 g/L $MgSO_4$ heptahydrate, 0.5 g/L $KH_2PO_4$, pH 7.0+25 µg/mL of spectinomycin). Oligonucleotides of SEQ ID NO: 5 through SEQ ID NO: 8 were used as primers in PCR to test for the presence of nondisrupted regions upstream and downstream of ThyA. Homologies to primers mapping within the ThyA coding region were from that part of the A. tumefaciens LBA4404 ThyA CDS that was deleted from the ThyA deletion clone (this region was cloned separately by PCR), and homologies to primers from the flanking regions were to C58 sequences located outside of the cloned upstream and downstream regions, so that PCR amplification would not proceed where the ThyA deletion derivative had inserted by homologous recombination. This was due to the large vector insertion that would accompany integration of the ThyA deletion derivative, separating the primer binding sites by several kilobases of DNA. DNA from each of the LBA4404 transformant candidates was tested, and *A. tumefaciens* LBA4404 DNA was used as a control template. The control gave PCR products of approximately the expected size in every reaction. For the fusion construct integration, only the upstream PCR reactions worked, indicating that the fusion construct integration event occurred downstream of ThyA.

The *A. tumefaciens* LBA4404 Thy deletion cointegrate strain was inoculated from a freshly streaked single colony on medium containing 50 µg/mL thymidine into 3 mL of AB minimal broth+50 µg/mL thymidine+/−trimethoprim (0, 500 and 1000 µg/mL in parallel cultures) and incubated at 28° C., 250 RPM for four days. The resulting visibly turbid cultures (approximately stationary phase) were subcultured by inoculation of 3 mL of fresh broth of the same type with 10 µL of the stationary culture. The diluted cultures were incubated with shaking as before, allowing the cultures to become visibly turbid after each dilution (typically three days). The dilution and re-culturing process was repeated through ten dilutions. Cultures in 1000 µg/mL of trimethoprim consistently produced some coagulated material suggestive of a stress response and cell lysis. Aliquots of 75 µL of the final stationary cultures in 500 µg/mL of trimethoprim and 150 µL of cultures in 1000 µg/mL of trimethoprim were plated on AB+50 µg/mL thymidine for replica plating and incubated at 28C. for three days. Replica plating was on AB minimal medium, AB+25 µg/mL spectinomycin and AB+50 µg/mL thymidine. Five colonies of the Thy deletion cointegrate strain were identified as failing to grow in the absence of thymidine, and were thus Thy deletion candidates. The presence of spectinomycin in the medium coupled with absence of thymidine gave even clearer results. The candidate ThyA deletion auxotrophs were purified by repeated suspending in sterile water and streaking on AB+50 µg/mL thymidine to obtain single colonies.

For two of the ThyA deletion candidates, PCR reactions on genomic DNA using SEQ ID NOS: 9 and 10 as primers exhibited only one PCR product of about 508 bp, indicative of a purified ThyA deletion construct in the absence of any wild type ThyA gene DNA, while the other candidates gave PCR products of about 1124 by and about 508 bp, indicative of the presence of both native ThyA and deletion ThyA sequences. Homologies to SEQ ID NOS: 9 and 10 are located in the upstream and downstream regions around ThyA, and the PCR reactions were predicted to give a PCR product of 508 by for the ThyA deletion derivative vs. approximately 1124 by for the native ThyA gene of *A. tumefaciens* LBA4404. The ThyA deletion candidates were confirmed to be unable to grow on AB minimal medium lacking thymidine, as well as on plates supplemented with 50 µg/mL thymidine+25 µg/mL spectinomycin. The candidates were also confirmed to test positively for production of ketolactose when cultured on lactose agar and exposed to Benedict's reagent, a test that is strongly indicative of *Agrobacterium*.

```
Primer
                                                 (SEQ ID NO: 1)
GGGGCTAACCGTAAGGACTTAGAGCGG Primer
                                                 (SEQ ID NO: 2)
GGGTTGAGGCGCATGGTCGGCAAGTCTCCGCGGTCGGAGCCGGTTTCCAT
CACATGCCGG Primer
                                                 (SEQ ID NO: 3)
CCGGCATGTGATGGAAACCGGCTCCGACCGCGGGAGAGCCTTGCCGACCAT
GCGCCTCAACCC Primer
                                                 (SEQ ID NO: 4)
CCCCTGCCCCCATGGGCCGCCACCGCCGCCC Primer
                                                 (SEQ ID NO: 5)
GCCGATGCCGTTTGCAAGTCAGC Primer
                                                 (SEQ ID NO: 6)
CATGGATGATCGAGCGCAGATGC Primer
                                                 (SEQ ID NO: 7)
TTGGTGACGCGCATATCTACGCC Primer
                                                 (SEQ ID NO: 8)
ATGATCTCTTCCAGATCGGGCGG Primer
                                                 (SEQ ID NO: 9)
TGCGGCAAGAAGCTTGGCGTGACCGATGACAG Primer
                                                 (SEQ ID NO: 10)
GTCAGTGGAAAGCTTCCAAGGCATATCGAGGTCG
```

Example 2

Vectors for Use in Auxotrophic *Agrobacterium* Strains

A strain of *Agrobacterium tumefaciens* LBA4404 auxotrophic for thymidine was transformed with the superbinary vector pSB1 (Komari et al, The Plant Journal (1996) 10(1): 165-174) using electroporation. The electroporated *Agrobacterium* cells were plated on minimal medium supplemented with 50 µg/ml thymidine (to support the auxotroph) and 2.5 µg/ml tetracycline (to select for the introduced pSB1 plasmid). The confirmed transformant was maintained as the target strain for plant transformation vectors. One such vector (PHP15303), carrying a ubiquitin promoter-driven GFP screenable marker gene cassette and a CaMV 35S promoter-driven BAR gene as selectable marker, was introduced into LBA4404(thy-)(pSB1), again using electroporation. *Agrobacterium* cells carrying the PHP15303/pSB1 cointegrate plasmid were identified by plating on minimal medium supplemented with 50 µg/ml thymidine and 50 µg/ml spectinomycin (to select for PHP15303). The cointegrate plasmid (PHP30894) was confirmed using a minimum of three diagnostic restriction digests. As a control, PHP15303 was also introduced into non-auxotrophic LBA4404 (pSB1). The resultant cointegrate plasmid was confirmed as above and designated PHP15325.

Example 3

Comparative Growth of Wild Type and Thymidine Auxotroph Under Unsupplemented Conditions Cells of LBA4404 (PHP15325) and LBA4404(thy⁻) (PHP30894) were grown in liquid minimal AB medium following typical bacterial protocols at 28° C. Thymidine was added at 5 mg/l to minimal AB for growth of the auxotroph.

Figure 3:
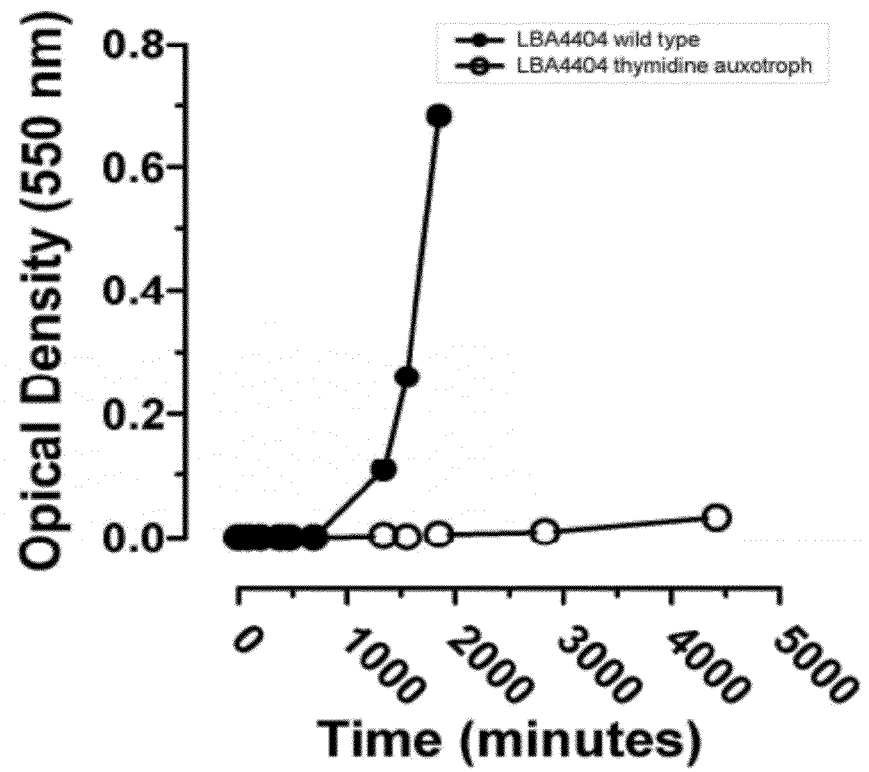
FIG. 3 is a graph showing the comparative growth of an *Agrobacterium* thymidine auxotroph and wild type *Agrobacterium* under unsupplemented conditions. As demonstrated in FIG. 3 and described in Example 3, the *Agrobacterium* thymidine auxotroph has limited growth when compared to a non-auxotrophic, prototrophic *Agrobacterium* of strain LBA4404 in the absence of thymidine.

When the bacterial cultures reached mid-log phase, they were collected by centrifugation, washed twice with unsupplemented minimal AB, and resuspended at $10^5$ CFU/ml in liquid minimal AB with varying thymidine supplementation. Growth of the cells over time was measured via optical density at 550 nm. The results are shown in FIG. 3 and demonstrate that without thymidine supplementation the LBA4404thy⁻ fails to grow.

Example 4

Transformation Experiment Using Thymidine Auxotroph

Maize transformation was practiced as detailed in Zhao and Ranch, *Transformation of Maize Via Agrobacterium tumefaciens Using a Binary Co-Integrate Vector System*, in *Plant Cell Culture Protocols*, V. Loyola-Vargas and F. Vazquez-Flota, Editors, Humana Press: Totowa N.J. p. 315-324 (2005). Two different strains of *Agrobacterium* were used; the wild-type, prototrophic, LBA4404(PHP15325) and a thymidine auxotroph of the same strain, LBA4404thy⁻ (PHP30894).

As shown in FIG. 5, the experiment was conducted with 10 ears of PHWWE embryo source material, with the embryos from an individual ear being distributed across three treatments. Treatment 1 was wild-type LBA4404, treatment two was LBA4404thy⁻ with no thymidine supplementation, treatment three was LBA4404thy⁻ with thymidine supplementation at 5 mg/l. As shown by this experiment, the auxotroph does not support transformation in the absence of thymidine. The frequency of transformation with the auxotroph, when thymidine is supplemented, is equivalent to the prototrophic LBA4404. The frequency of single copy transgenic events is the same regardless of which *Agrobacterium* was used to produce the events, and the average seed production by events produced from either the wild-type or auxotrophic *Agrobacterium* were indistinguishable.

Example 5

Thymidine Auxotroph is not an Evident Contaminant of Plant Tissue

Maize transformation is practiced as detailed in Zhao, Z., et al., *Transformation of Maize Via Agrobacterium tumefaciens Using a Binary Co-Integrate Vector System*, in *Plant Cell Culture Protocols*, V. Loyola-Vargas and F. Vazquez-Flota, Editors, Humana Press: Totowa N.J. p. 315-324 (2005), except proprietary inbred genotype PHWWE is used, and no counter-selective antibiotic was used after infection to cure the plant tissue. Wild-type *Agrobacterium tumefaciens* LBA4404 (PHP15325) and a thymidine auxotroph of *Agrobacterium tumefaciens* LBA4404thy⁻ (PHP38094) were used for transformation. The experimental protocols are shown in FIG. 4. In the trial with wild-type *Agrobacterium*, within 10 days after initial exposure to the *Agrobacterium*, all the treated embryos were engulfed by overgrowth of contaminating, unrestrained, *Agrobacterium*. In contrast, 46 days after infection of the immature embryos with the auxotrophic *Agrobacterium*, there was no evidence of bacterial growth by any remaining viable auxotrophic *Agrobacterium*. On a culture medium that is permissive to rapid growth of the wild type *Agrobacterium*, and in the presence of plant tissue, the auxotrophic *Agrobacterium* failed to proliferate and contaminate the plant tissue.

Example 6

Transformation Experiment Using Thymidine Auxotroph with Inbred PHRO3 Maize Immature Embryos Maize inbred PHRO3 immature embryos were transformed with two different strains of *Agrobacterium*; the wild-type, prototrophic, LBA4404 (PHP32269) and a thymidine auxotroph of the same strain, LBA4404thy⁻ (PHP38332), each containing the T-DNA cassette UBI-UBI 5UTR-UBI intron1::marker::PINII-UBI-UBI 5UTR-UBI intron1::MO-PAT::ZS-Yellow1 N1:PINII.

The experiment was conducted with 8 ears of PHRO3 embryo source material, with the embryos from each individual ear being distributed across the two treatments. Treatment one was transformation with the prototrophic LBA4404 (PHP32269), treatment two was transformation with the thymidine auxotroph LBA4404thy-(PHP38332) with thymidine supplementation at 50 mg/l during infection and coculture only. The transformation frequency, measured by number of callus colonies recovered from each treatment divided by the total number of immature embryos treated, was 37.9% (91/240) using LBA4404 and 36.3% (87/240) using LBA4404thyA-. Chi-square indicates that these frequencies cannot be resolved as different. The frequency of transformation with the auxotroph, when thymidine is supplemented in infection and coculture only, is equivalent to the prototrophic LBA4404 with inbred PHRO3 immature maize embryos.

| Ear ID | # embryos | vector | # events | % Tx callus | # embryos | vector | # events | % Tx callus |
|---|---|---|---|---|---|---|---|---|
| 1 | 30 | 32269 | 7 | 23.3 | 30 | 38332 | 7 | 23.3 |
| 2 | 30 | 32269 | 5 | 16.7 | 30 | 38332 | 4 | 13.3 |
| 3 | 30 | 32269 | 13 | 43.3 | 30 | 38332 | 1 | 3.3 |
| 4 | 30 | 32269 | 19 | 63.3 | 30 | 38332 | 16 | 53.3 |
| 5 | 30 | 32269 | 20 | 66.7 | 30 | 38332 | 17 | 56.7 |
| 6 | 30 | 32269 | 6 | 20.0 | 30 | 38332 | 22 | 73.3 |
| 7 | 30 | 32269 | 6 | 20.0 | 30 | 38332 | 9 | 30.0 |
| 8 | 30 | 32269 | 15 | 50.0 | 30 | 38332 | 11 | 36.7 |
| total | 240 | 32269 | 91 | 37.9 | 240 | 38332 | 87 | 36.3 |

Example 7

Transformation Experiment Using Thymidine Auxotroph with F1 Hybrid Maize Immature Embryos Maize transformation was practiced as detailed in Zhao and Ranch, *Transformation of Maize Via Agrobacterium tumefaciens Using a Binary Co-Integrate Vector System*, in *Plant Cell Culture Protocols*, V. Loyola-Vargas and F. Vazquez-Flota, Editors, Humana Press: Totowa N.J. p. 315-324 (2005) and U.S. Pat. No. 7,022,894 with F1 hybrid maize embryos. Two different strains of *Agrobacterium* were used in this test; the wild-type, prototrophic, LBA4404 (PHP34978) and a thymidine auxotroph of the same strain, LBA4404thy- (PHP34979). The selectable marker is moPAT, and bialaphos was used as the selection agent. The T-DNA cassette for each was LTP2 PRO_DS-RED2_PINIITERM// GZ-W64A PRO_ZM-ODC-22 (TR2)_ADH1 INTRON6_ZM-ODC-22 (TR2)//OLE PRO_ZM-ODC-22 (TR2)_ADH1 INTRON1 (PHI)_ZM-ODC-22 (TR2)_NOS TERM//UBI1ZM PRO_UBI1ZM 5UTR(PHI)_UBI1ZM INTRON1 (PHI)_MO-PAT_PINII TERM.

The experiment was conducted with 12 ears of High type II X PH17AW embryo source material, with the embryos from an individual ear being distributed across two treatments. Treatment one was transformation with the prototrophic LBA4404 (PHP34978), treatment two was transformation with the thymidine auxotroph LBA4404thy-(PHP34979) with thymidine supplementation at 5 mg/l during infection and coculture only. The transformation frequency, measured by number of herbicide resistant callus colonies recovered from each treatment divided by the total number of immature embryos treated, was 36% (176/480) and 33% (151/450), respectively. Chi-square indicates that these frequencies cannot be resolved as different. The frequency of transformation with the auxotroph, when thymidine is supplemented in infection and coculture only, is equivalent to the prototrophic LBA4404 with F1 hybrid immature maize embryos.

We claim:

1. A method of transforming and regenerating a plant cell expressing a transgene, without an *Agrobacterium* counter-selective agent, comprising:
   contacting a plant cell with an *Agrobacterium* that is a thymidine auxotroph, in the presence of thymidine or thymine necessary for the auxotrophic *Agrobacterium's* survival, proliferation or growth, wherein said auxotroph comprises a transgene;
   co-cultivating the plant cell with the thymidine auxotroph in the presence of thymidine or thymine;
   selecting in the absence of an *Agrobacterium* counter-selective agent for the transformed cell expressing the transgene, and in the absence of thymidine or thymine; and
   regenerating from the selected transformed plant cell a plant expressing the transgene, in the absence of an *Agrobacterium* counter-selective agent and in the absence of thymidine or thymine;
   wherein the thymidine auxotrophic *Agrobacterium* comprises a disrupted thyA gene which encoded thymidylate synthase prior to disruption.

2. The method of claim 1, wherein the thymidine auxotrophic *Agrobacterium* comprises a thyA gene disrupted by deletion, partial deletion, knock out, insertion, or an introduction of one or more mutations in the gene.

3. The method of claim 2, wherein the thyA gene is disrupted by way of a frame shift mutation, homologous recombination or any combination thereof.

4. The *Agrobacterium* of claim 1, wherein the *Agrobacterium* is *Agrobacterium tumefaciens, rhizogenes* or *radiobacter*.

5. The *Agrobacterium* of claim 1, wherein the *Agrobacterium* is *Agrobacterium* strain LBA4404, EHA101, C58, EHA105, AGL1, or GV3101.

6. The method of claim 1, wherein the plant cell is within an immature embryo.

7. The method of claim 1, wherein the plant cell comprises a sorghum, maize, rice, wheat, soybean, sunflower, canola, alfalfa, barley, or millet cell.

8. The method of claim 1, wherein the counter-selective agent is an antibiotic or herbicide.

9. The method of claim 1, wherein the counter-selective agent comprises carbenicillin, cefotaxime, silver nitrate, vancomycin, piperacillin, ticarcillin, ceftazidime, cefbuperazone, cefminox, moxalactam, flomoxef, aztreonam, carumonam, or meropenem.

10. A method of biologically containing transgenic *Agrobacterium* during plant regeneration, the method comprising:
    transforming a plant cell using an *Agrobacterium* that is a thymidine auxotroph, wherein the plant cell is transformed in the absence of an *Agrobacterium* counter-selective agent and in the presence of thymidine or thymine, and wherein the auxotrophic *Agrobacterium* comprises a transgene; and
    regenerating in the absence of an *Agrobacterium* counter-selective agent and in the absence of thymidine or thymine, the transformed plant cell into a transformed plant that expresses the transgene, thereby biologically containing the transgenic *Agrobacterium*;
    wherein the thymidine auxotrophic *Agrobacterium* comprises a disrupted thyA gene which encoded thymidylate synthase prior to disruption.

11. The method of claim 10, wherein the thymidine auxotrophic *Agrobacterium* comprises a thyA gene disrupted by deletion, partial deletion, knock out, insertion, or an introduction of one or more mutations in the gene.

12. The method of claim 11, wherein the thyA gene is disrupted by way of a frame shift mutation, homologous recombination or any combination thereof.

13. The method of claim 10, wherein the plant cell is within an immature embryo.

14. The method of claim 10, wherein the plant cell is a sorghum, maize, rice, wheat, soybean, sunflower, canola, alfalfa, barley, or millet cell.

15. The method of claim 10, wherein the counter-selective agent is an antibiotic or herbicide.

16. The method of claim 10, wherein the counter-selective agent comprises carbenicillin, cefotaxime, vancomycin, piperacillin, ticarcillin, ceftazidime, cefbuperazone, cefminox, moxalactam, flomoxef, aztreonam, carumonam, or meropenem.

17. An isolated *Agrobacterium* auxotroph wherein a thyA gene encoding thymidylate synthase has been disrupted, and wherein said auxotroph exhibits the inability to survive, proliferate or grow in the absence of thymine or thymidine.

18. The *Agrobacterium* of claim 17, wherein the thyA gene has been disrupted by deletion, partial deletion, knock out, insertion, or an introduction of one or more mutations in the gene.

19. The *Agrobacterium* of claim 18, wherein the thyA gene is disrupted by way of a frame shift mutation, homologous recombination or any combination thereof.

20. The *Agrobacterium* of claim 17, wherein the *Agrobacterium* is *Agrobacterium tumefaciens, rhizogenes* or *radiobacter*.

21. The *Agrobacterium* of claim 17, wherein the *Agrobacterium* is *Agrobacterium* strain LBA4404, EHA101, C58, EHA105, AGL1, or GV3101.

22. A method of producing an *Agrobacterium* thymidine auxotroph comprising:
    constructing a nucleic acid construct comprising a knock-out of the thyA gene or a fragment thereof;
    contacting the nucleic acid construct with the chromosomal DNA of the *Agrobacterium* comprising a wild-type thyA gene under conditions that permit homologous recombination between the nucleic acid construct and the wild-type thyA gene; and
    selecting the *Agrobacterium* under conditions that permit selection of *Agrobacterium* having the nucleic acid construct integrated into the *Agrobacterium* chromosomal DNA, thereby producing an *Agrobacterium* thymidine auxotroph exhibiting the inability to survive, proliferate or grow without thymidine or thymine.

23. The method of claim 22, further comprising selecting an *Agrobacterium* that is *Agrobacterium* thymidine auxotroph by exposing the candidate auxotrophic *Agrobacterium* to an environment that lacks thymine or thymidine and determining the growth, proliferation or survival of the candidate auxotrophic *Agrobacterium*.

24. The method of claim 22, wherein all or part of the *Agrobacterium* wild type thyA gene is removed from the *Agrobacterium* chromosome by homologous recombination.

25. The method of claim 22, wherein the nucleic acid construct comprises at least two sequences that are homologous to all or part of the wild type thyA gene to enable integration by homologous recombination.

26. The method of claim 25, wherein the at least two sequences of the nucleic acid construct flank all or part of the wild type thyA gene.

27. The method of claim 26, wherein the at least two sequences of the nucleic acid construct are linked to a selectable marker.

28. The method of claim 27, wherein the selectable marker confers antibiotic resistance.

29. The method of claim 28, wherein the selectable marker confers resistance to carbenicillin, chloramphenicol, kanamycin, ampicillin, erythromycin, spectinomycin or tetracycline.

30. The method of claim 22, wherein the *Agrobacterium* is *Agrobacterium tumefaciens, rhizogenes* or *radiobacter*.

31. The method of claim 22, wherein the *Agrobacterium* is *Agrobacterium* strain LBA4404, EHA101, C58, EHA105, AGL1, or GV3101.

32. An isolated *Agrobacterium* thymidine auxotroph produced by the method of claim 22.

* * * * *

```
                        SEQUENCE LISTING

<160> NUMBER OF SEQ ID NOS: 11

<210> SEQ ID NO 1
<211> LENGTH: 27
<212> TYPE: DNA
<213> ORGANISM: Artificial sequence
<220> FEATURE:
<223> OTHER INFORMATION: Description of artifical sequence: primer for
      PCR amplification of ThyA-encoding gene of Agrobacterium
      tumefaciens.

<400> SEQUENCE: 1
ggggctaacc gtaaggactt agagcgg                                        27

<210> SEQ ID NO 2
<211> LENGTH: 60
<212> TYPE: DNA
<213> ORGANISM: Artificial sequence
<220> FEATURE:
<223> OTHER INFORMATION: Description of artifical sequence: primer for
      PCR amplification of ThyA-encoding gene of Agrobacterium
      tumefaciens.

<400> SEQUENCE: 2
gggttgaggc gcatggtcgg caagtctccg cggtcggagc cggtttccat cacatgccgg    60

<210> SEQ ID NO 3
<211> LENGTH: 62
<212> TYPE: DNA
<213> ORGANISM: Artificial sequence
<220> FEATURE:
<223> OTHER INFORMATION: Description of artifical sequence: primer for
      PCR amplification of ThyA-encoding gene of Agrobacterium
      tumefaciens.

<400> SEQUENCE: 3
ccggcatgtg atggaaaccg gctccgaccg cggagagcct tgccgaccat gcgcctcaac    60
cc                                                                  62

<210> SEQ ID NO 4
<211> LENGTH: 31
<212> TYPE: DNA
<213> ORGANISM: Artificial sequence
<220> FEATURE:
```

-continued

<223> OTHER INFORMATION: Description of artifical sequence: primer for
    PCR amplification of ThyA-encoding gene of Agrobacterium
    tumefaciens.

<400> SEQUENCE: 4
cccctgcccc catgggccgc caccgccgcc c                                       31

<210> SEQ ID NO 5
<211> LENGTH: 23
<212> TYPE: DNA
<213> ORGANISM: Artificial sequence
<220> FEATURE:
<223> OTHER INFORMATION: Description of artifical sequence: primer for
    PCR amplification to test for the presence of nondisrupted regions
    upstream and downstream of ThyA-encoding gene of Agrobacterium
    tumefaciens.

<400> SEQUENCE: 5
gccgatgccg tttgcaagtc agc                                                23

<210> SEQ ID NO 6
<211> LENGTH: 23
<212> TYPE: DNA
<213> ORGANISM: Artificial sequence
<220> FEATURE:
<223> OTHER INFORMATION: Description of artifical sequence: primer for
    PCR amplification to test for the presence of nondisrupted regions
    upstream and downstream of ThyA-encoding gene of Agrobacterium
    tumefaciens.

<400> SEQUENCE: 6
catggatgat cgagcgcaga tgc                                                23

<210> SEQ ID NO 7
<211> LENGTH: 23
<212> TYPE: DNA
<213> ORGANISM: Artificial sequence
<220> FEATURE:
<223> OTHER INFORMATION: Description of artifical sequence: primer for
    PCR amplification to test for the presence of nondisrupted regions
    upstream and downstream of ThyA-encoding gene of Agrobacterium
    tumefaciens.

<400> SEQUENCE: 7
ttggtgacgc gcatatctac gcc                                                23

<210> SEQ ID NO 8
<211> LENGTH: 23
<212> TYPE: DNA
<213> ORGANISM: Artificial sequence
<220> FEATURE:
<223> OTHER INFORMATION: Description of artifical sequence: primer for
    PCR amplification to test for the presence of nondisrupted regions
    upstream and downstream of ThyA-encoding gene of Agrobacterium
    tumefaciens.

<400> SEQUENCE: 8
atgatctctt ccagatcggg cgg                                                23

<210> SEQ ID NO 9
<211> LENGTH: 32
<212> TYPE: DNA
<213> ORGANISM: Artificial sequence
<220> FEATURE:
<223> OTHER INFORMATION: Description of artifical sequence: primer for
    PCR amplification to test for the presence of nondisrupted regions
    upstream and downstream of ThyA-encoding gene of Agrobacterium
    tumefaciens.

<400> SEQUENCE: 9
tgcggcaaga agcttggcgt gaccgatgac ag        32

<210> SEQ ID NO 10
<211> LENGTH: 34
<212> TYPE: DNA
<213> ORGANISM: Artificial sequence
<220> FEATURE:
<223> OTHER INFORMATION: Description of artifical sequence: primer for
      PCR amplification to test for the presence of nondisrupted regions
      upstream and downstream of ThyA-encoding gene of Agrobacterium
      tumefaciens.

<400> SEQUENCE: 10
gtcagtggaa agcttccaag gcatatcgag gtcg        34

<210> SEQ ID NO 11
<211> LENGTH: 1792
<212> TYPE: DNA
<213> ORGANISM: Agrobacterium tumefaciens

<400> SEQUENCE: 11

| | | |
|---|---|---|
| cgaattcccg caccgccatt aggcagcgag agcgtattcc ttagcgttgt tgtcatttgc | 60 |
| aactacactt gtgacccgat aacggcggta tcatgccgag caaaagttcg atctttacgc | 120 |
| ccttgtcgat cctatttcgc ccccatcaaa agccggcctt catcttcaaa agccgccggt | 180 |
| ttttggtgga ggcgccgggt accgccccg ggtccaatag gtttattaca ccgaccgttt | 240 |
| atcgccatag ccgggttgcc ccggcaaggt tcatataggc gtttcccttg ccgagaaaa | 300 |
| ggggccgatg acaattccat gaaaagattt cgtgtttgcc gcccacaatt tagacaattc | 360 |
| ttgacgacga gggattgctg acacattctc cctacaaccg gtcaccacaa gcaacaccgg | 420 |
| gccggggaca cacgaaggag tggacatgac tgactatctc gcagatgtga agaaatacga | 480 |
| cgcagcagcc gacgaagcga ttgtcggcaa gatcgtcaaa catctcggca ttgccctgcg | 540 |
| caaccgggat tcatcgttgg tgtccgcttc cgatccggaa gagcttgcac gtgtgaaggc | 600 |
| gaactggtgc ggcaagaagc ttggcgtgac cgatgacagc gccgacaagg cgatcgatgc | 660 |
| aaccgccaag gccatggccg cagaccgctc caagtcgcgt gtgacgtttt attatctggt | 720 |
| ggccaaggaa ctgggcaaac tccagtcgct ctgattttt ggcggggata agcgacccgc | 780 |
| tggtgattgg ttctgtcgcc ctgtgttatt atattccctt gatatcaggg aatcggcggc | 840 |
| agaacacatg aaacaatatc tcgatcttct ccggcatgtg atggaaaccg gctccgaccg | 900 |
| cggagagcct tgccgaccat gcgcctcaac ccggatgtac gagacctctt ctcctttaag | 960 |
| ttcgaagact ttacgctgga gaactacgag gcggattcaa ccatcaaggc accgatcgcg | 1020 |
| gtatgagcga gccgcgcatc accatcatcg tcgcggtgtc ggaaaacggc gttatcggcc | 1080 |
| gcgacctcga tatgccttgg aagctttcca ctgacctaaa gcgcttcaag gcgatgacga | 1140 |
| tgggcaaacc gctcatcatg ggcaggaaga catttctctc ggtgggcgag cgtccattgc | 1200 |
| cgggccggcc gcacatcatc gtcagccgca atgccgatta caggcctgat ggcgtggatg | 1260 |
| tcgtgtcgtc gcttgaagac gccctcgcgc ttggcaaaag caaggctgcg gaactgggtg | 1320 |
| tggacgaggt tttcgttgcc ggtggcgggg aaatctaccg tcaggccatg ccgtttgccg | 1380 |
| atcaactttc cgtcacccat gtggccgtaa agcttgatgg cgacactttt tttccggaaa | 1440 |
| tcgatcccgc cgtctttgaa aaaatcgagg aaaatgccgt tcccgccggg gaaaaggaca | 1500 |
| attatccggt tctgttcacc acttatttgc gcagagccgc gtcaaagtga actatttacc | 1560 |
| ctgattgggt atttagttac cacctctgcg ttgaaacgca cgcttctcct tcttataacg | 1620 |

```
ggtccatatt cccgccgcac gcgagcaatc gctttcgaac gggatcggga gaggctttta    1680
taaagaggta ttgatgccct ggagcaatca gaatggcggc ggcggcccct ggggcggcgg    1740
cggtggtggc ggaaacaacc agggcggcgg tggcggccca tggaggcagg gg            1792
```